United States Patent [19]

Kaneko et al.

[11] Patent Number: 5,573,705
[45] Date of Patent: Nov. 12, 1996

[54] SILACYCLOHEXANE COMPOUND, A METHOD OF PREPARING IT AND A LIQUID CRYSTAL COMPOSITION CONTAINING IT

[75] Inventors: Tatsushi Kaneko; Takeshi Kinsho; Takaaki Shimizu; Tsutomu Ogihara; Ryuichi Saito, all of Niigata-ken; Hideshi Kurihara, Kawasaki, all of Japan

[73] Assignee: Shin-Etsu Chemical Co., Ltd., Tokyo, Japan

[21] Appl. No.: 362,964

[22] Filed: Dec. 23, 1994

[30] Foreign Application Priority Data

Dec. 24, 1993 [JP] Japan ................................ 5-347889

[51] Int. Cl.⁶ .............................. C09K 19/34; C07F 7/08
[52] U.S. Cl. ........................ 252/299.61; 556/406
[58] Field of Search ...................... 252/299.61; 556/406

[56] References Cited

U.S. PATENT DOCUMENTS 2,607,791  8/1952  Goodwin ........................ 556/406 X
5,302,734  4/1994  Jung et al. ........................ 556/406

FOREIGN PATENT DOCUMENTS 0355008  2/1990  European Pat. Off. .

*Primary Examiner*—C. H. Kelly
*Attorney, Agent, or Firm*—Townsend & Banta

[57] ABSTRACT

A liquid crystal composition comprising a silacyclohexane compound represented by the following formula (I):

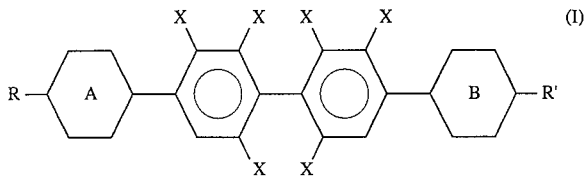

wherein R and R' denote an alkyl group, a mono- or di-fluoroalkyl group, an alkoxyalkyl group or an alkenyl group; at least one of

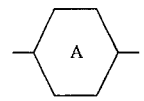

and

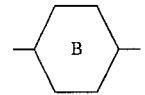

denotes a silacyclohexylene group whose silicon at positions 1 or 4 has a substitutional group of H, F, Cl of $CH_3$, and the other denotes a silacyclohexylene group whose silicon at positions 1 or 4 has a substitutional group of H, F, Cl or $CH_3$ or a cyclohexylene group; and 0–2 of the substitutional groups X on the aromatic rings denote F and the remaining X's denote H.

3 Claims, No Drawings

SILACYCLOHEXANE COMPOUND, A METHOD OF PREPARING IT AND A LIQUID CRYSTAL COMPOSITION CONTAINING IT

BACKGROUND OF THE INVENTION

1. Field of the Invention

This invention relates to a new silacyclohexane compound, a method of preparing it, and a liquid crystal composition which contains it, as well as a liquid crystal display element which contains said liquid crystal composition.

2. The Prior Art

A liquid crystal display element utilizes the optical anisotropy and dielectric anisotropy of liquid crystal substances. Display modes include the TN mode (twisted nematic mode), the STN mode (super twisted nematic mode), the SBE mode (super birefringence mode), the DS mode (dynamic scattering mode), the guest-host mode, the DAP mode ("deformation of aligned phase" mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required by all display methods. Furthermore, it is desirable for the liquid crystal material to have a low viscosity, and also to have a short address time, low threshold voltage and high contrast in the cell(s).

Currently, there is no single compound which satisfies all these requirements. In practice, liquid crystal mixtures are obtained by mixing several to more than ten liquid crystal compounds and latent liquid crystal compounds. Because of this, it is also important that the components of a liquid crystal composition mix easily.

Among liquid crystal compounds which can be these components, one of the basic components conventionally known which, in particular, control the ability to assume the liquid crystal phase at high temperatures is a compound which has the cyclohexyl ring-biphenyl-cyclohexyl ring structure, a so-called CBC structure, such as

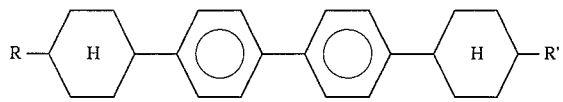

(Japanese examined patent publication (Tokko) Sho 62-46527),

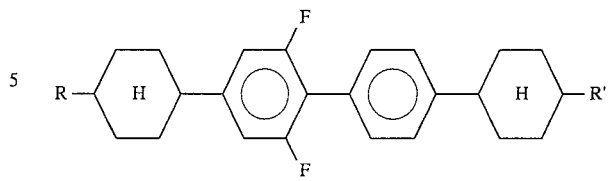

(Tokko Hei 4-28693),

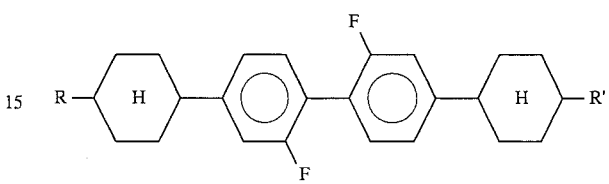

(Tokko Hei 4-28693), and

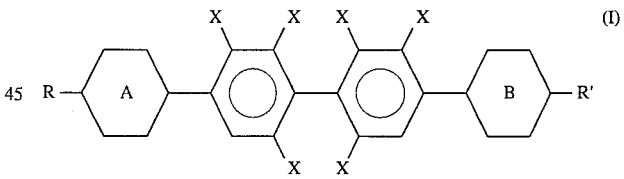

(Tokko Hei 4-28693) have been known.

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

From such a viewpoint, this invention is a newly developed liquid crystal substance targeting improvement in the characteristics of liquid crystal substances, and its object is to provide a liquid crystal compound containing silacyclohexane rings, which is completely different from the conventional liquid crystal compounds with the aforementioned cyclohexyl ring-biphenyl-cyclohexyl ring structure (CBC structure).

That is, this invention is a silacyclohexane compound represented by the following general formula (I).

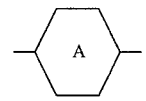

In this formula, R and R' denote a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

For

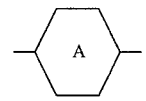

and

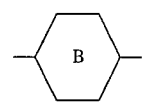

at least one of the two denotes a trans-1-sila-1, 4-cyclohexylene or a trans-4-sila-1, 4-cyclohexylene group whose silicon at position 1 or position 4 has a substitutional group(s) of H, F, Cl or CH₃. For the substitutional groups X on the aromatic rings, there are 0, 1 or 2 F's and the remaining ones are H's.

This invention is also a method of preparing the silacyclohexane compound as described in claim 1 characterized by the use of a carbon-carbon bond formation reaction in the presence of a transition metal compound catalyst between an organometallic reagent

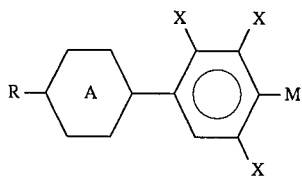

(R is the same as in the general formula (I), M denotes MgP (P denotes a halogen atom), ZnP or B (OY)₂ (Y is H or an alkyl group), and X denotes F or H) and an aryl halide compound

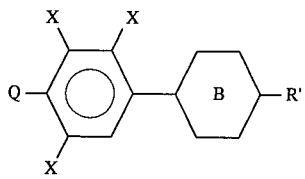

(R' is the same as in the general formula (I), and Q denotes a halogen atom).

Furthermore, this invention is a liquid crystal composition characterized by containing the compound as represented by the general formula (I) and a liquid crystal display element which uses this composition.

This invention is described in detail below.

DETAILED DESCRIPTION

The new compounds represented by said general formula (I) are silacyclohexane compounds whose ring structure has at least one trans-1 or trans-4-silacyclohexane ring, specifically represented by the general formulas shown below:

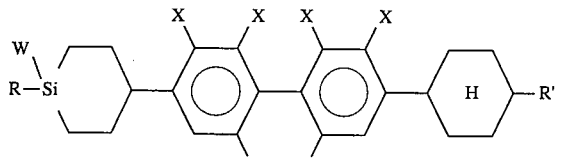

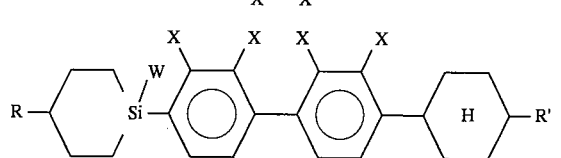

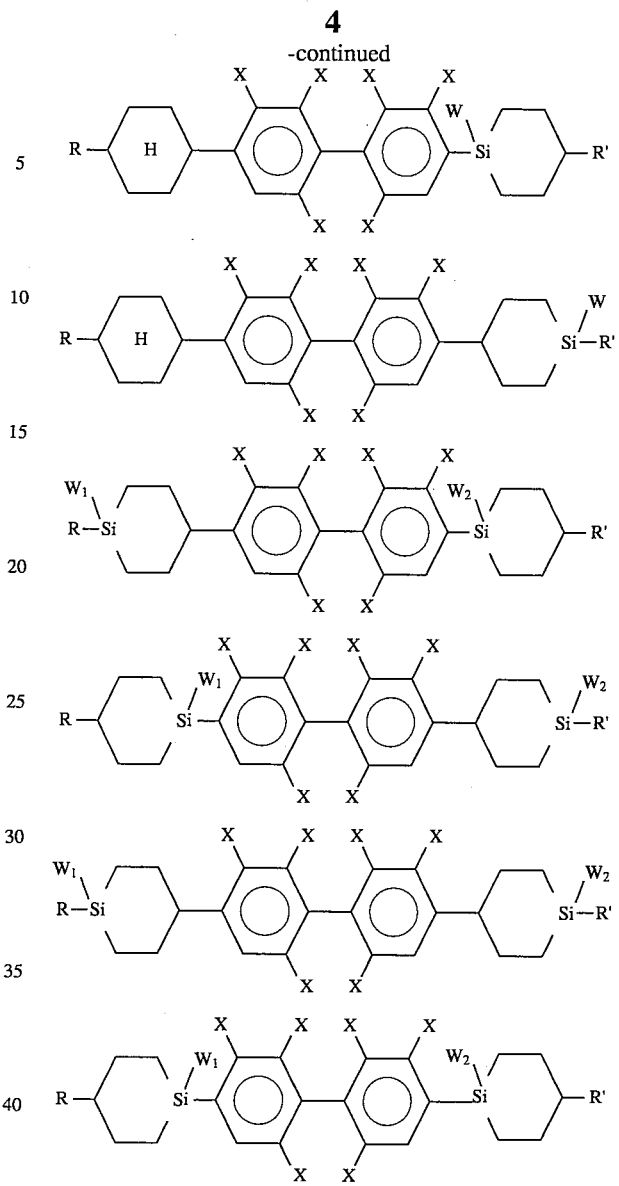

In these formulas, R and R' denote the following groups listed in (a) through (e):

(a) A linear-chain alkyl group with a carbon number of 1–10, i.e. a methyl, ethyl, n-propyl, n-butyl, n-pentyl, n-hexyl, n-heptyl, n-octyl, n-nonyl or n-decyl group (b) A branched-chain alkyl group with a carbon number of 3–8, i.e. an isopropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl or 3-methylheptyl group (c) An alkoxyalkyl group with a carbon number of 2–7, i.e. a methoxymethyl, ethoxymethyl, propoxymethyl, butoxymethyl, pentoxymethyl, methoxyethyl, ethoxyethyl, propoxyethyl, butoxyethyl, methoxypropyl, ethoxypropyl, propoxypropyl, methoxybutyl, ethoxybutyl, methoxypentyl or ethoxypentyl group (d) An alkenyl group with a carbon number of 2–8, i.e. a vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl or 7-octenyl group (e) A mono- or di-fluoroalkyl group with a carbon number of 1–10, i.e. fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorooctyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1, 1-difluoroethyl, 1, 1-difluoropropyl, 1, 1-difluorobutyl, 1, 1-difluoropentyl, 1, 1-difluorohexyl, 1, 1-difluoroheptyl, 1, 1-difluorooctyl, 1, 1-difluorononyl, 1, 1-difluorodecyl, 2, 2-difluoroethyl, 2, 2-difluoropropyl, 2, 2-difluorobutyl, 2, 2-difluoropentyl, 2, 2-difluorohexyl, 2, 2-difluoroheptyl, 2, 2-difluorooctyl, 2, 2-difluorononyl, 2, 2-difluorodecyl, 3, 3-difluoropropyl, 3, 3-difluorobutyl, 3, 3-difluoropentyl, 3, 3-difluorohexyl, 3, 3-difluoroheptyl, 3, 3-difluorooctyl, 3, 3-difluorononyl, 3, 3-difluorodecyl, 4, 4-difluorobutyl, 4, 4-difluoropentyl, 4, 4-difluorohexyl, 4, 4-difluoroheptyl, 4, 4-difluorooctyl, 4, 4-difluorononyl, 4, 4-difluorodecyl, 5, 5-difluoropentyl, 5, 5-difluorohexyl, 5, 5-difluoroheptyl, difluorooctyl, 5, 5-difluorononyl, 5, 5-difluorodecyl, 6, 6-difluorohexyl, 6, 6-difluoroheptyl, 6, 6-difluorooctyl, 6, 6-difluorononyl, 6, 6-difluorodecyl, 7, 7-difluoroheptyl, 7, 7-difluorooctyl, 7, 7- -difluorononyl, 7, 7-difluorodecyl, 8, 8-difluorooctyl, 8, 8-difluorononyl, 8, 8-difluorodecyl, 9, 9-difluorononyl or 10, 10 -difluorodecyl group H, F and $CH_3$ groups are desirable for W, $W_1$ and $W_2$ in practical use.

The manufacturing methods of these compounds are described next. These compounds are prepared using a reaction between an organometallic reagent and an aryl halide compound. A detailed description is given below.

the organometallic reagent

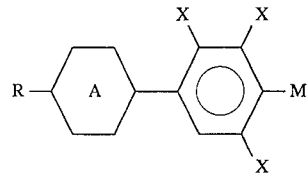

(R is the same as in the general formula (I), M denotes MgP (P denotes a halogen atom), ZnP or B $(OY)_2$ (Y is H or an alkyl group) can be easily prepared from the corresponding halide

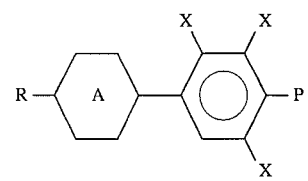

(P denotes a halogen atom). For example, the reaction path shown below can be used.

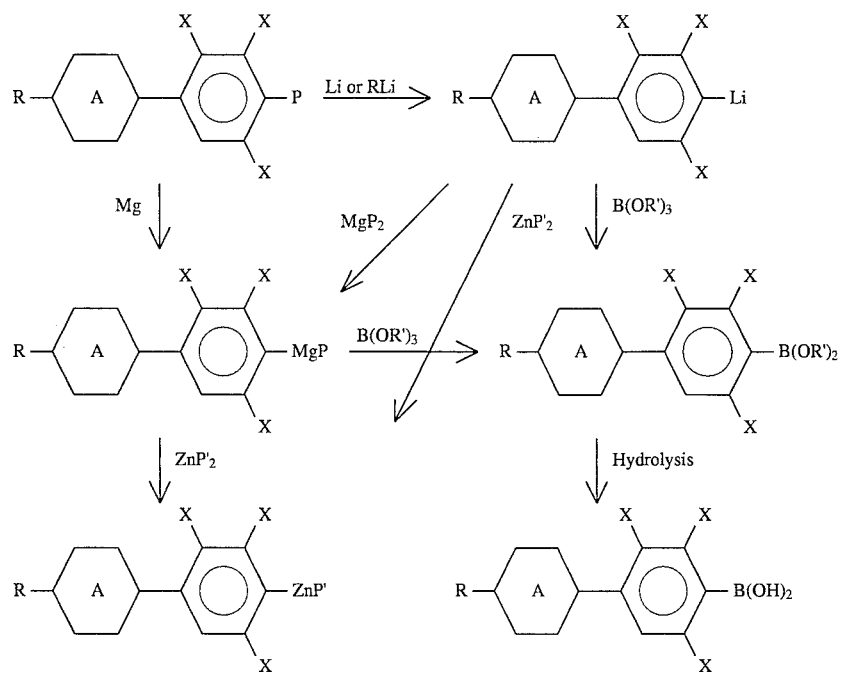

(P and P' denote halogen atoms.)

It is also possible to directly ortho-lithiate

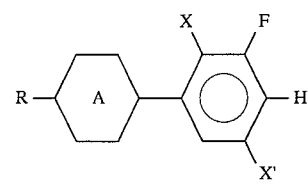

(X and X' denote H or F) by using a reaction with alkyl lithium, thus synthesize a compound

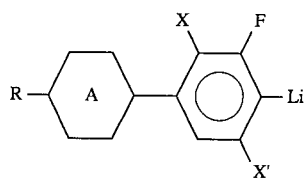

and then follow the synthesis path described above.

The organometallic reagent thus generated is then brought into reaction with the aryl halide compound

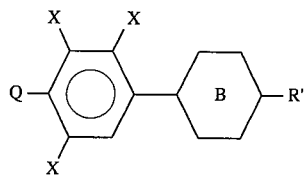

in the presence of a transition metal catalyst to obtain

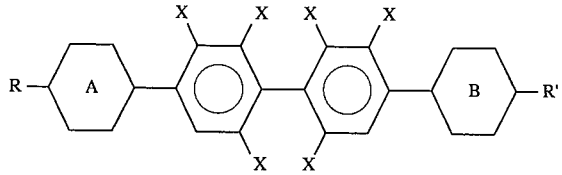

For the catalyst, palladium and nickel compounds are preferable. Examples of the palladium catalysts are zero-valent palladium compounds such as tetrakis (triphenylphosphine) palladium (0) and di [1,2-bis (diphenylphosphino) ethane] palladium (0), and compounds composed of palladium and a ligand(s) such as palladium acetate and palladium chloride, as well as a combination of these and a reducing agent.

Examples of the nickel catalysts are divalent nickel compounds such as 1, 3-bis (diphenylphosphino) propane nickel (II) chloride, 1, 2-his (diphenylphosphino) ethane nickel (II) chloride and his (triphenylphosphine) nickel (II) chloride, and zero-valent nickel compounds such as tetrakis (triphenylphosphine) nickel (0).

When the organometallic reagent is a boric acid derivative, i.e. when M is B (OY)$_2$, the reaction should preferably be carried out in the presence of a base. For the base, for example, inorganic bases such as sodium carbonate, sodium bicarbonate, potassium carbonate, sodium hydroxide and potassium hydroxide, and organic bases such as triethylamine, tributylamine and dimethylaniline can be used.

Following a conventional after treatment, the reaction product is purified by means of recrystallization, chromatography and such to obtain the silacyclohexane compound of this invention represented by the general formula (I).

The silacyclohexane compound of this invention can be mixed with known compounds to obtain a liquid crystal composition. The compound used for mixing to obtain the liquid crystal compound can be chosen from among the known compounds shown below

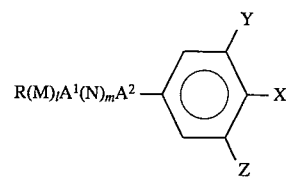

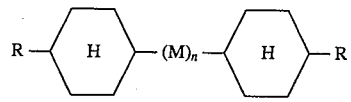

In the above formulas, (M) and (N) denote one of the following items a) through e):

a) A trans-1, 4-cyclohexylene group which has no substitution or which has one or more substitutional groups such as F, Cl, Br, CN or alkyl groups b) A ring that has 0 or S substituted for one or nonadjacent two CH$_2$ groups in the cyclohexane ring c) A 1,-4-cyclohexenylene group d) A 1, 4-phenylene group which has no substitution or which has one or two substitutional groups such as F, Cl, CH$_3$ or CN groups e) A ring that has an N atom substituted for one or two CH groups in a 1, 4-phenylene group.

A$^1$ and A$^2$ each denote —CH$_2$CH$_2$—, —CH=CH—, —C≡C—, —CO$_2$—, —OCO—, —CH$_2$O—, —OCH$_2$— or a single bond.

l, m=0, 1 or 2 (where l+m=1, 2 or 3, and n=0, 1 or 2).

R denotes hydrogen, a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon number of 2–8.

X denotes a CN, F, Cl, CF$_3$, OCF$_3$, OCHF$_2$, R or OR group. Y denotes H or F. Z denotes H or F.

In the above description, if l=2 and n=2, then (M) can contain heterogeneous rings, and if m=2, then (N) can contain heterogeneous rings.

The ratio of one or more types of the silacyclohexane compound of this invention contained in the liquid crystal composition is 1–50 wt %. more preferably 5–30 wt %. The liquid crystal composition can also contain a polygenetic dye(s) to generate a colored guest-host system and additives to change the dielectric anisotropy, viscosity and the orientation of the nematic phase.

The liquid crystal composition thus formed can be used to manufacture various liquid crystal display elements in conventional methods. That is, the liquid crystal composition containing the silacyclohexane compound of this invention is sealed between transparent plates which have electrodes of desired shapes and is thus used as liquid crystal display elements. This element can have various undercoatings, overcoatings for orientation control, a polarizer plate(s), a filter(s) and a reflector layer(s), as necessary. It can be made into a laminated cell or combined with other display elements. Semiconductor substrates and light sources can also be used to make various types of displays.

For the driving method of the liquid crystal display element, prior-art methods in the industry of liquid crystal display elements, such as the dynamic scattering (DSM) method, the twisted nematic (TN) method and the guest-host (GH) method can be adopted.

EXAMPLE

The details of this invention are described below by referring to specific examples.

[EXAMPLE 1]

Preparation of trans, trans-4, 4'-di (4-n-pentyl-4-silacyclohexyl) biphenyl 110 ml of a THF-toluene (1:1) solution of 1.0M organozinc reagent, prepared by reacting trans-4-(p-iodophenyl)-1-n-pentyl-silacyclohexane with magnesium metal and then with zinc chloride, was dripped into a mixture of 37.2 g (100 mmol) of trans-4-(p-iodophenyl)-1-n-pentyl-1-silacyclohexane, 100 mg of tetrakis (triphenylphosphine) palladium (0) and 200 ml of tetrahydrofuran (hereafter referred to as "THF"). Following a conventional after treatment, the product was purified by means of chromatography to obtain 36.8 g of the target product (yield 75%).

IR ν max: 2916, 2850, 2100, 1452, 1404, 1078, 924, 885, 833 and 810 $cm^{-1}$ (KBr tablet method) S-I transition temperature: 168.2° C.

The following target products were obtained in the same manner as Example 1.

[EXAMPLE 2]

Trans, trans-4, 4'-di (4-n-propyl-4-silacyclohexyl) biphenyl

IR ν max: 2918, 2852, 2100, 1903, 1497, 1456, 985, 810 and 532 $cm^{-1}$ (KBr disc)

S1-S2 transition temperature: 95.5° C.

S2-I transition temperature: 173.7° C.

[EXAMPLE 3]

Trans, trans-4-(4-n-pentyl-4-silacyclohexyl)-4'-(4-n-propyl-4-silacyclohexyl) biphenyl IR ν max: 2916, 2850, 2100, 1902, 1497, 1460, 1005, 812 and 536 $cm^{-1}$ (KBr disc) S-N transition temperature: 191.9° C. N-I transition temperature: 231.9° C.

[EXAMPLE 4]

trans, trans-4-(4-n-pentyl-1-silacyclohexyl)-4'-(4-n-propyl-1-silacyclohexyl) biphenyl

[EXAMPLE 5]

trans, trans-2-fluoro-4, 4'-di (4-n-pentyl-4-silacyclohexyl) biphenyl

[EXAMPLE 6]

trans, trans-2-fluoro-4-(4-n-pentyl-4-silacyclohexyl)-4'-(4-n-pentylcyclohexyl) biphenyl IR ν max: 2920, 2848, 2100, 1491, 1404, 1194, 987, 887 and 814 $cm^{-1}$ (KBr disc) C-S transition temperature: 71.3° C. S-N transition temperature: 137.2° C. N-I transition temperature: 225.4° C.

[EXAMPLE 7]

trans, trans-2'-fluoro-4-(4-n-pentyl-4-silacyclohexyl)-4'-(4-n-propylcyclohexyl) biphenyl IR ν max: 2953, 2918, 2850, 2100, 1491, 1404, 985, 887, 879, 818 and 582 $cm^{-1}$ (KBr disc) C-S transition temperature: 51.6° C. S-N transition temperature: 89.9° C. N-I transition temperature: 232.6° C.

[EXAMPLE 8]

trans, trans-2'-fluoro-4-(4-n-pentyl-4-silacyclohexyl)-4'-(4-n-pentylcyclohexyl) biphenyl IR ν max: 2953, 2922, 2850, 2102, 1493, 1446, 1404, 986, 887, 814 and 584 $cm^{-1}$ (KBr disc) C-S transition temperature: 69.9° C. S-N transition temperature: 131.2° C. N-I transition temperature: 230.7° C.

[EXAMPLE 9]

trans, trans-2'-fluoro-4-(4-n-propyl-4-silacyclohexyl)-4'-(4-n-propylcyclohexyl) biphenyl IR ν max: 2955, 2922, 2850, 2098, 1493, 1404, 984, 887 and 812 $cm^{-1}$ (KBr disc) C-S transition temperature: 110.8° C. S-N transition temperature: 118.4° C. N-I transition temperature: 259.3° C.

[EXAMPLE 10]

trans, trans-2'-fluoro-4-(4-n-propyl-4-silacyclohexyl)-4'-(4-n-pentylcyclohexyl) biphenyl IR ν max: 2953, 2922, 2850, 2100, 1493, 1446, 1404, 984, 887 and 812 $cm^{-1}$ (KBr disc) C-S transition temperature: 53.5° C. S-N transition temperature: 116.8° C. N-I transition temperature: 246.5° C.

[EXAMPLE 11]

trans, trans-2-fluoro-4-(4-n-propyl-4-silacyclohexyl)-4'-(4-n-propylcyclohexyl) biphenyl IR ν max: 2955, 2920, 2848, 2104, 1491, 1404, 1194, 986, 889 and 814 $cm^{-1}$ (KBr disc) C-S transition temperature: 112.9° C. N-I transition temperature: 239.8° C.

[EXAMPLE 12]

trans, trans-2-fluoro-4-(4-n-propyl-4-silacyclohexyl)-4'-(4-n-pentylcyclohexyl) biphenyl IR ν max: 2955, 2922, 2850, 2110, 1491, 1404, 1194, 986, 889 and 818 $cm^{-1}$ (KBr disc) C-S transition temperature: 49.6° C. S-N transition temperature: 104.8° C. N-I transition temperature: 250.1° C.

[EXAMPLE 13]

trans, trans-2-fluoro-4-(4-n-pentyl-4-silacyclohexyl)-4'-(4-n-propylcyclohexyl) biphenyl IR ν max: 2955, 2920, 2850, 2102, 1446, 1404, 1194, 987, 887 and 814 $cm^{-1}$ (KBr disc) C-S transition temperature: 79.0° C. S-N transition temperature: 95.0° C. N-I transition temperature: 247.0 ° C.

[EXAMPLE 14]

trans, trans-4-(1-methyl-4-n-pentyl-1-silacyclohexyl)- 4'-(4-n-pentylcyclohexy) biphenyl

[EXAMPLE 15]

trans, trans-4-(4-isopentyl-4-silacyclohexyl)-4'-(4-n-pentylcyclohexyl) biphenyl

[EXAMPLE 16]

Preparation of trans, trans-4-(4-n-propyl-4-silacyclohexyl)-4'-(4-n-propylcyclohexyl) biphenyl 24.7 g (100 mmol) of trans-4-(4-n-propylcyclohexyl) phenylboric acid (prepared by reacting the corresponding Grignard's reagent with trimethylboric acid followed by hydrolysis using 10% hydrochloric acid) was added to a mixture of 34.4 g (100 mmol) of trans-4-(p-iodophenyl)-1-n-propyl-l-silacyclohexane, 12.0 g (119 mmol) of triethylamine, 100 mg of tetrakis (triphenylphosphine) palladium (0) and 200 ml of N,N-dimethylformamide, and a reaction was carried out at 100° C. for 3 hours. Following a conventional after treatment, the product was purified by means of chromatography to obtain 26.0 g of the target product (yield 62%).

IR ν max: 2918, 2104, 1902, 1497, 1444, 984, 810 and 532 cm$^{-1}$ (KBr disc) S-N transition temperature: 191.6° C. N-I transition temperature: 274.7° C.

The following compounds were obtained in the same manner as Example 16.

[EXAMPLE 17]

trans, trans-4-(4-n-pentyl-4-silacyclohexyl)-4'-(4-n-propylcyclohexyl) biphenyl

IR ν max: 2918, 2102, 1903, 1497, 1446, 986, 812 and 536 cm$^{-1}$ (KBr disc) S-N transition temperature: 197.9° C. N-I transition temperature: 252.2° C.

[EXAMPLE 18]

trans, trans-4-(4-n-pentylsilacyclohexyl)-4'-(4-n-pentylcyclohexyl) biphenyl

IR ν max: 2956, 2920, 2850, 2104, 1498, 1456, 985, 887 and 812 cm$^{-1}$ (KBr disc) S-N transition temperature: 203.7° C. N-I transition temperature: 214.1° C.

[EXAMPLE 19]

trans, trans-4-(4-n-propyl-4-silacyclohexyl)-4'-(4-n-propylcyclohexyl) biphenyl

IR ν max: 2920, 2102, 1903, 1497, 1446, 986, 812 and 536 cm$^{-1}$ (KBr disc) S-N transition temperature: 177.9° C. N-I transition temperature: 210.4° C.

[EXAMPLE 20]

trans, trans-4-(4-n-propyl-4-silacyclohexyl)-4'-{4-(4-fluoropropylcyclohexyl)} biphenyl

[EXAMPLE 21]

trans, trans-4-{4-(4-fluoropentyl-4-silacyclohexyl)-4'-(4-n-pentylcyclohexyl) biphenyl

[EXAMPLE 22]

trans, trans-4-(4-(5-methoxypentyl)-4-silacyclohexane}-4'-(4-n-propylcyclohexyl) biphenyl The compounds of this invention obtained in the examples described above were added to existing liquid crystal compositions to prepare liquid crystal compositions of this invention.

[EXAMPLE 23]

A liquid crystal mixture comprising 34% of 2-(trans-4-n-pentylcyclohexyl)-1-(3,4-difluorophenyl) ethane, 15% of 1, 2-difluoro-4-[trans-4-(trans-4-n-propylcyclohexyl) cyclohexyl] benzene and 51% of 2-[trans-4-(trans-4-propylcyclohexyl) cyclohexyl]-1-(3, 4-difluorophenyl) ethane exhibits the nematic liquid crystal phase in the temperature range of −17° to 63° C. A liquid crystal mixture comprising 85% of this mixture and trans, trans-4-(4-n-propyl-4-silacyclohexyl)-4'-(4-n-propylcyclohexyl) biphenyl obtained in Example 11 exhibits the nematic liquid crystal phase in the extended temperature range of −24 to 94.8° C.

As described thus far, this invention can provide liquid crystal compounds with Si as a ring composing element which have the nematic liquid crystal phase extended into a high temperature region. Conventionally, such compounds have been unknown. By using these compounds as components of a liquid crystal composition, the liquid crystal phase can be extended into a high temperature region.

The liquid crystal compounds of this invention, depending on the selection of substitutional groups, can be widely used as the base material which comprises the major component of the liquid crystal phase, in a manner similar to how the conventional liquid crystal compounds with a CBC structure of similar hydrocarbon rings are used. The liquid crystal compounds of this invention are useful for manufacturing the liquid crystal phase for displays based on the dynamic scattering (DS) or deformation of aligned phase (DAP mode) as well as the liquid crystal phase used in display elements based on the twisted nematic cell or the cholesteric-nematic phase transition.

We claim:

1. A silacyclohexane compound represented by the following formula (I):

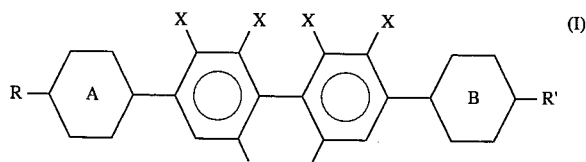

wherein R and R' denote a linear-chain alkyl group with a carbon number of 1–10, a mono- or di-fluoroalkyl group with a carbon number of 1–10, a branched-chain alkyl group with a carbon number of 3–8, an alkoxyalkyl group with a carbon number of 2–7, or an alkenyl group with a carbon numer of 2–8; wherein at least one of

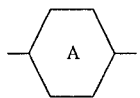

and

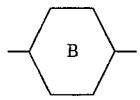

denotes a trans-1-sila-1, 4-cyclohexylene or a trans-4-sila-1, 4-cyclohexylene group whose silicon at positions 1 or 4 has a substititional group of H, F, Cl or $CH_3$, and the other denotes a trans-1-sila-1, 4-cyclohexylene or a trans-4-sila-1, 4cyclohexylene group whose silicon at positions 1 or 4 has a substitutional group of H, F, Cl or $CH_3$, or a trans-1, 4-cyclohexylene group; and neither 0–2 of the substitutional groups X on the aromatic rings are F and the remaining X's are H's.

2. A liquid crystal composition comprising the silacyclohexane compound of claim 1.

3. A liquid crystal display element comprising the liquid crystal composition of claim 2.

* * * * *